US008758841B2

(12) United States Patent
Hayashi et al.

(10) Patent No.: US 8,758,841 B2
(45) Date of Patent: Jun. 24, 2014

(54) CHEESE CAPABLE OF DISINFECTING HELICOBACTER PYLORI

(75) Inventors: Shunji Hayashi, Odawara (JP); Shigeru Aizawa, Odawara (JP); Naoki Taketomo, Odawara (JP); Tadashi Nakatsubo, Odawara (JP); Noriaki Matsunaga, Odawara (JP); Katsunori Kimura, Odawara (JP)

(73) Assignee: Meiji Co., Ltd., Tokyo (JP)

( * ) Notice: Subject to any disclaimer, the term of this patent is extended or adjusted under 35 U.S.C. 154(b) by 1412 days.

(21) Appl. No.: 10/510,497

(22) PCT Filed: Apr. 11, 2003

(86) PCT No.: PCT/JP03/04649
§ 371 (c)(1),
(2), (4) Date: Oct. 7, 2004

(87) PCT Pub. No.: WO03/086093
PCT Pub. Date: Oct. 23, 2003

(65) Prior Publication Data
US 2005/0163888 A1 Jul. 28, 2005

(30) Foreign Application Priority Data

Apr. 12, 2002 (JP) ................................ P2002-111083
Jul. 23, 2002 (JP) ................................ P2002-213338

(51) Int. Cl.
A23C 9/12 (2006.01)

(52) U.S. Cl.
USPC ........................................................ 426/42

(58) Field of Classification Search
USPC ............ 426/36, 61, 42; 424/93.45; 435/252.9
See application file for complete search history.

(56) References Cited

U.S. PATENT DOCUMENTS

| 3,852,158 A | * | 12/1974 | Anderson et al. .......... 435/253.6 |
| 5,908,646 A | * | 6/1999 | Mayra-Makinen et al. .... 426/36 |
| 2002/0037341 A1 | | 3/2002 | Lee et al. |

FOREIGN PATENT DOCUMENTS

| CA | 2274535 A1 | 7/1998 |
| CN | 1306400 A | 1/2001 |
| EP | 1 112 692 A | 7/2001 |
| JP | 60-075233 A | 4/1985 |
| JP | 07-236484 A | 9/1995 |
| JP | 08-116872 A | 5/1996 |
| JP | 2001-000143 A | 1/2001 |
| JP | 2001-002578 A | 1/2001 |
| KR | 10-1991-0004797 A | 3/1991 |
| WO | WO 98/27825 A1 | 7/1998 |
| WO | WO 01 88150 A | 11/2001 |

OTHER PUBLICATIONS

Gardiner, G. et al. 1998. Development of a probiotic cheddar cheese containing human-derived Lactobacillus paracasei strains. Appl. Environ. Microbiol. 64(6): 2192-2199.*
DE-1955833—Storage-stable cheese products. Abstract.*
Elli, M. et al. 1999. Growth requirements of Lactobacillus johnsonii in skim and UHT milk. International Dairy J. 9:507-513.*
International Search Report dated Jul. 30, 2003.
Abstract of JP-A-2001-002578, Published Sep. 1, 2001, Meiji Milk Products Company LT.; Wakamoto Pharma. Co., Ltd. (JP); Patent Abstracts of Japan, vol. 2000, No. 16, May 8, 2001.
Frank V. Kosikowski et al., "Cheese and Fermented Milk Foods" (1999) Third Edition Second Printing, vol. II, Ch. 10, pp. 114-117.
G. van den Berg et al., "Gouda and Related Cheeses", Cheese: Chemistry, Physics and Microbiology, (2004) Third Edition, vol. 2, pp. 103-116.
Chinese Office Action dated Dec. 2, 2005.
Ichiko Sakamoto et al., "Suppressive Effect of Lactobacillus gasseri OLL2716 (LG 21) on Helicobater pylori Infection in Human", Journal of Antimicrobial Chemotherapy, 2001, pp. 709-710, vol. 47, The British Society for Antimicrobial Chemotherapy.
Taiwanese Office Action dated Jun. 26, 2008.
Canadian Office Action dated Jun. 9, 2009.
Office Action dated Aug. 25, 2010 from the Taiwanese Patent Office in Taiwanese counterpart application No. 092108354.
Korean Intellectual Property Office, Communication dated Jul. 12, 2011 in a counterpart Korean patent application No. 10-2010-7008725.

* cited by examiner

*Primary Examiner* — Larry Tarazano
*Assistant Examiner* — Hamid R Badr
(74) *Attorney, Agent, or Firm* — Sughrue Mion, PLLC

(57) ABSTRACT

Natural cheese which comprises a lactic acid bacterium belonging to Lactobacillus gasseri having a disinfection potency against Helicobacter pylori, and a method for producing the natural cheese.

3 Claims, 9 Drawing Sheets

CHEESE CAPABLE OF DISINFECTING HELICOBACTER PYLORI

FIELD OF THE INVENTION

The present invention relates to natural cheese containing *Lactobacillus gasseri* (hereinafter sometimes referred to as "*L. gasseri*") having a disinfection potency against *Helicobacter pylori* (hereinafter sometimes referred to as "*H. pylori*") and/or a protection property against infection with *H. pylori*. Particularly, the present invention relates to natural cheese which maintains a high survival bacterial count of *L. gasseri* even when the cheese is preserved at a low temperature over a time of 6 months or longer.

BACKGROUND ART

Since *H. pylori* was found as a bacterium living in the stomach by Warren et al. in 1983 (*Lancet*, I. 1273 (1983)), attentions have been paid to the relationship between *H. pylori* and chronic gastritis, gastric ulcer and duodenal ulcer. Recently, it has been found that gastric gland cancer is caused in mongolian gerbil infected with *H. pylori* without administering any carcinogens (Watanabe et al., *Gastroenterology*, 115, 642 (1988)), and thus the relation of *H. pylori* with gastric cancer as a causal bacterium has also been suggested. In addition, it has been increasingly clarified that the recurrence of peptic ulcer in *H. pylori*-positive patients with peptic ulcer can be prevented by disinfecting *H. pylori*. Various methods for disinfecting *H. pylori* from the stomach have been studied.

In order to disinfect gastric *H. pylori* without using antibiotics, a method using *Lactobacillus gasseri* OLL 2716 (*L. gasseri* OLL 2716) having a high disinfection potency against *H. pylori* (which has been deposited on Jan. 14, 2000 as Accession No. FERM BP-6999 in National Institute of Bioscience and Technology, Agency of Industrial Science and Technology (Higashi 1-1-3, Tsukuba, Ibaraki, Japan) [present name: International Patent Organism Depositary, National Institute of Advanced Industrial Science and Technology (AIST Tsukuba Central 6, 1-1, Higashi 1-Chome Tsukuba-shi, Ibaraki-ken, Japan)] (also called "LG21") has been proposed (JP-A-2001-143 and EP 1 112 692 A1). The *Lactobacillus gasseri* strain OLL 2716 was found as the result of screening studies on a large number of lactobacillus bacteria derived from human intestines, a bacterial strain having the following characteristics: (1) high resistance to gastric acid; (2) good growth under low pH conditions; (3) high potency to suppress the adherence of *H. pylori* onto human gastric cancer cell MKN45; (4) high potency to suppress the growth of *H. pylori* during co-culture with *H. pylori* in mixture; (5) high potency to disinfect *H. pylori* when dosed in *H. pylori*-infected model mouse; and (6) high survival, good flavor and physical properties when applied to food products. Particularly, since the strain is excellent in production properties (preservability, flavor and physical properties) in preparing fermented milk, it is preferable to administer the strain in the form of fermented milk. Thus, disinfection of *H. pylori* using the antibacterial effect of lactobacillus can be considered as a convenient and effective method without any side effects. However, fermented milk has a relatively short quality preservation period of about 2 weeks due to food properties of fermented milk. After 2 weeks preservation, the bacterial count decreases to almost half the level before preservation. Namely, fermented milk is not suitable for long preservation.

DISCLOSURE OF THE INVENTION

An object of the present invention is to provide a food product in which *L. gasseri* having a high disinfection potency against *H. pylori* and a protection property against infection with *H. pylori* can survive at a high bacterial count during preservation over a long time and which can be taken as part of a daily diet without discomfort.

The present invention relates to the following (1) to (10):

(1) Natural cheese which comprises a lactic acid bacterium belonging to *Lactobacillus gasseri* having a disinfection potency against *Helicobacter pylori*.

(2) The natural cheese according to (1), wherein the lactic acid bacterium is resistant to low pH environment.

(3) The natural cheese according to (1) or (2), wherein the lactic acid bacterium is *Lactobacillus gasseri* OLL 2716 (FERM BP-6999) or a mutant thereof.

(4) The natural cheese according to any of (1) to (3), wherein the lactic acid bacterium is present at a viable count of $10^7$ cfu/g or more when preserved at a temperature of 10° C. or less for 6 months.

(5) A food which comprises the natural cheese according to any one of (1) to (4).

(6) A process for producing the natural cheese according to any one of (1) to (4), which comprises:
adding a yeast extract to a milk component before formation of a curd.

(7) The process according to (6), wherein the curd is incubated without being cooled after molding and pressing.

(8) The process according to (6) or (7), wherein the curd is incubated at 20 to 35° C. for 16 to 26 hours.

(9) The process according to any one of (6) to (8), wherein a lactic acid bacterium belonging to *Lactobacillus gasseri* having a disinfection potency against *Helicobacter pylori* is added to raw milk as a starter.

(10) The process according to any one of (6) to (9), wherein the lactic acid bacterium is *Lactobacillus gasseri* OLL 2716 (FERM BP-6999) or a mutant thereof.

BEST MODE FOR CARRYING OUT THE INVENTION

Figure 1:
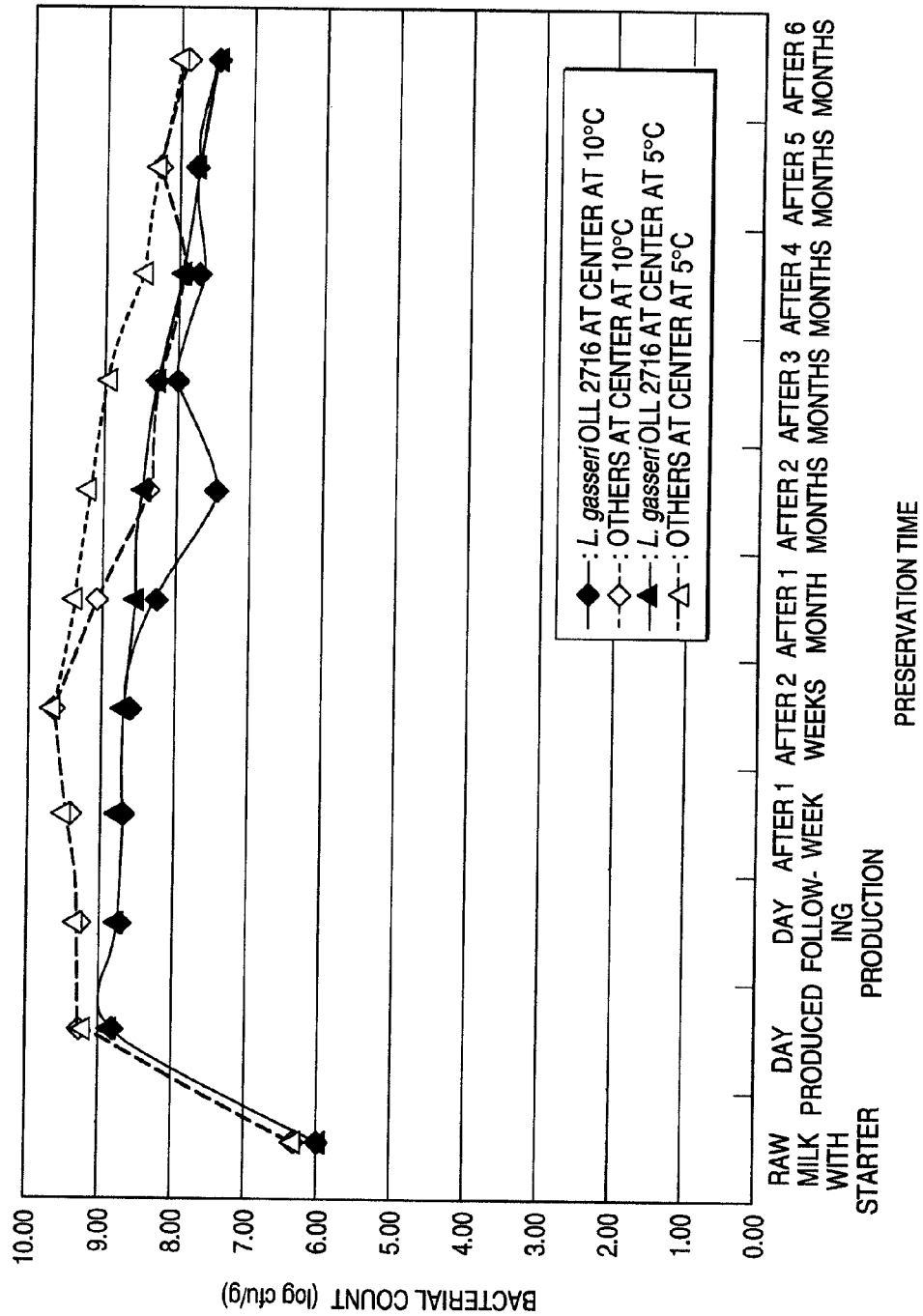
FIG. 1 shows bacterial count changes in *L. gasseri*-containing cheddar cheese (Example 1).

In the description, percentage (%) is by weight unless otherwise indicated.

In order to solve the above-described problems, the present inventors have conducted intensive studies. As a result, they have found that *L. gasseri* can grow at a sufficient amount and can survive at a high concentration over a long time in natural cheese by employing such a novel constitution that viable cells of *L. gasseri* OLL 2716 having a disinfection potency against *H. pylori* and a protection property of infection with *H. pylori* are kept in natural cheese. Moreover, they have found for the first time that when addition of a yeast extract and/or incubation of a cheese curd after molding and pressing are carried out in addition to the commonly employed process for producing cheese, unexpectedly *L. gasseri* grows and survives in cheese dominantly over lactic acid bacteria for cheese. Thus, the present invention has been completed based on these findings.

The present invention is explained below in detail.

The natural cheese of the present invention is preferably solid hard type or semi-hard type natural cheese such as cheddar cheese, gouda cheese, edam cheese, string cheese and mozzarella cheese.

Raw milk for producing the natural cheese of the present invention is selected from those generally used for the production of cheese. Examples include milk of mammals such as cow, goat, sheep, water buffalo, horse and yak; materials derived from milk such as cream, skim milk, partly skim milk, whole fat milk, concentrated milk, concentrated skim milk, reducing milk which is obtained by dissolving skim milk etc. in water, and whey; and the like. They may be used alone or in combination thereof.

The natural cheese of the present invention comprises a lactic acid bacterium belonging to *Lactobacillus gasseri* having a disinfection potency against *H. pylori* (hereinafter referred to the "*L. gasseri* of the present invention"). The *L. gasseri* of the present invention has a disinfection potency against *H. pylori*, and preferably has a high disinfection potency against *H. pylori*. The disinfection potency against *H. pylori* means that the *L. gasseri* has a potency of suppressing the growth of *H. pylori*, and preferably, when the *L. gasseri* is administered into the stomach containing *H. pylori*, the number of *H. pylori* can be decreased below the detectable limit such as $1 \times 10^3$ colony forming units (hereinafter referred to as "cfu")/g of stomach contents.

The *L. gasseri* of the present invention is preferably resistant to low pH environment. Specifically, the *L. gasseri* of the present invention has high gastric acid resistance in human or nonhuman animal stomach environment, growing well under conditions at low pH and being capable of disinfecting *H. pylori* and protecting hosts against infection with *H. pylori* by the administration of viable cells of the *L. gasseri* of the present invention in the form of natural cheese to thereby prevent the onset or recurrence of gastritis or gastric or duodenal ulcer. Also, in order to resist the acidic environment of the human gastrointestinal tract, the *L. gasseri* of the present invention should be resistant to acidic conditions between pH 7 and pH 2, although the optimum pH of generally used lactic acid bacteria is 6 to 7. Survival and growth of the *L. gasseri* of the present invention in cheese having a pH of 5 to 7 has been confirmed. Furthermore, the *L. gasseri* of the present invention is preferably a high viable count when orally administered, such as $10^7$ cfu/g cheese, more preferably $10^9$ cfu/g cheese.

As the lactic acid bacterium of the present invention, *L. gasseri* OLL 2716 (FERM BP-6999) is preferably used. Furthermore, a mutant of *Lactobacillus gasseri* OLL 2716 (FERM BP-6999) is included in the lactic acid bacterium of the present invention, so long as the mutant has a disinfection potency against *H. pylori* and is nontoxic to a human or a non-human animal. The mutant can be prepared by subjecting *Lactobacillus gasseri* OLL 2716 (FERM BP-6999) to an appropriate mutation treatment, such as exposure to ultraviolet light, X-ray or radiation, and a chemical treatment with a mutagenic compound (e.g., nitrosoguanidine, acridine dye), and can also be prepared by insertion, deletion or substitution of nucleotides, as well as spontaneous mutation.

When the natural cheese of the present invention is preserved at a temperature of 10° C. or less for 6 months, the *L. gasseri* of the present invention is especially viable at a viable count of $10^7$ cfu/g or more. The natural cheese of the present invention is preferably preserved for maturing at a temperature of 10° C. or less, more preferably at a temperature of 2° C. to 10° C., if necessary, with cooling under anaerobic conditions. The time for the maturing is decided depending on the kind of the cheese. Also, the 6 months are counted from the date after the incubation of the cheese curd after molding and squeezing is finished. As a matter of course, the natural cheese in which the *L. gasseri* is viable at a viable count of $10^7$ cfu/g or more when preserved at a temperature of 10° C. or less for longer than 6 months is included in the present invention. Furthermore, since the *L. gasseri* of the present invention has no problem in terms of safety, the maximum viable count is not particularly limited.

In general, processes for producing natural cheese contain steps common to all types of cheese, i.e., pretreatments such as standardization and sterilization of raw milk, production of curd and subsequent finishing procedures. The kind of starter, fermentation conditions, curd treatments, methods for adding salt and preservation, and the like may vary depending on the kind of cheese. In the production of the natural cheese of the present invention, *L. gasseri* is preferably added as a *L. gasseri* starter, and the *L. gasseri* starter can be used together with a lactic acid bacteria starter for cheese, and in addition to the commonly employed process suitable for producing various cheeses, a yeast extract is added to a milk component before formation of a curd, and/or the cheese curd is incubated after molding and pressing. The milk component before formation of a curd may be raw milk as described above or may contain any additives, so long as a curd is not formed.

The *L. gasseri* starter is a lactic acid bacterium belonging to *L. gasseri* which has a disinfection potency against *H. pylori* as described in the above, and is preferably *L. gasseri* OLL 2716 (FERM BP-6999).

*L. gasseri* OLL 2716 (FERM BP-6999) can be prepared from a stock culture via plural steps including production of a mother starter and a bulk starter. Also, a concentrated starter (a frozen or freeze-dried product) having a high bacterial count which is inoculated directly for producing the bulk starter or the product without preparing the mother starter can be used.

The amount of the *L. gasseri* starter added to the raw milk can be optionally determined depending on the purpose of use (prevention, health or therapeutic treatment) and production conditions. When an object is to disinfect *H. pylori*, it is preferable to take the natural cheese in such an amount that viable cells at a final amount of about $10^9$ cfu (9.0 log cfu) are taken in per day. Thus, the amount of the *L. gasseri* starter added to the raw milk may be determined so as to give a daily natural cheese intake per human or a non-human animal containing viable cells in an amount corresponding to the level as described above. However, each of the *L. gasseri* starter and a lactic acid bacteria starter which are prepared in a method described in Example of the present invention are preferably added to the raw milk from 0.5 to 5%, more preferably 1%, per kg of the raw milk, to take each of *L. gasseri* viable cells and lactic acid bacteria viable cells at a final amount of about $10^6$ to $10^7$ cfu. The *L. gasseri* starter is preferably added to milk component immediately after the step of cooling, since the earlier it is added, the more *L. gasseri* increases.

Next, a process for producing the natural cheese of the present invention is described in detail using cheddar cheese as an example.

A typical process for producing cheddar cheese is known, in which (1) raw milk is standardized, sterilized and cooled; (2) a lactic acid bacteria starter is added to the raw milk in (1), followed by mixing; (3) calcium chloride and rennet are added to the resulting mixture in (2) to thereby coagulate the milk and form a curd; (4) the curd obtained in (3) is cut and cooked to thereby remove whey; (5) after cheddaring and milling the curd, dry salt is added to the curd, followed by stirring; and (6) the curd is molded, vacuum-packed and matured.

Based on the above process, the natural cheese of the present invention can be produced by, for example, a method in which (1) 40 kg of raw milk is sterilized at 63° C. for 30 minutes and then cooled down to 32° C.; (2) 400 g of a lactic acid bacteria starter for cheese (*Lactobacillus lactis* subsp. *lactis*) and 400 g of a *L. gasseri* starter are added to the raw milk in (1); (3) 4 g of calcium chloride and 0.1 g of rennet are added to the resulting mixture in (2) and is allowed to stand for 45 minutes; (4) the thus obtained curd is cut into pieces of about 8 mm in width, stirred for 20 minutes, heated to 40° C. within 40 minutes, stirred for 60 minutes and precipitated for 5 minutes, and then whey is removed for 15 minutes; (5) after cheddaring for 2 hours, the curd is milled into thumb-size pieces and 80 g of salt is added; and (6) the curd is packed into 2 molds of 2 kg in size, pressed for 2 hours, vacuum-packed and matured. In this process, it is especially preferable that a yeast extract is added to a milk component in any of (1) to (3) before formation of the curd, and/or the curd is incubated after the molding and pressing in (6).

A method of preparing the lactic acid bacteria for cheese and the *L. gasseri* bulk starter described above is described as an example of the present invention. First, one of the lactic acid bacterium strains for cheese and a stock of *L. gasseri* are each precultured under activation in a 10% skim milk medium containing a yeast extract over 3 generations. Next, the lactic acid bacteria starter for cheese is inoculated at a ratio of 1% into a 10% skim milk medium, while the *L. gasseri* starter is inoculated at a ratio of 1% into a 10% defatted powder milk medium containing 0.1% yeast extract. The lactic acid bacteria is cultured at 25° C. for 16 hours and the *L. gasseri* starter is cultured at 35° C. for 24 hours, thereby giving respective bulk starters.

For growth of *L. gasseri* in the natural cheese dominantly over lactic acid bacteria for cheese, a yeast extract is preferably added before pressing of a curd, is more preferably added to a milk component before formation of a curd. The yeast extract is preferably added in an amount of from 0.05 to 0.2%, and more preferably from 0.08 to 0.15% per liter of a milk component. As a yeast extract, any product sold under the product classification "yeast extract" can be used. For example, trade name "meast P2G" by Asahi Breweries, Ltd is available.

Furthermore, the survival ratio of *L. gasseri* in the natural cheese can be improved by incubating the curd after the molding and pressing. The incubation is preferably carried out, for example, without cooling immediately after the molding and pressing. Furthermore, the incubation is carried out at 20 to 35° C. for 16 to 26 hours, preferably at 22 to 28° C. for 19 to 24 hours.

The *L. gasseri* in the natural cheese of the present invention before the molding and pressing is preferably at a viable count of from $10^8$ to $10^9$ cfu per gram of the natural cheese, and the number of *L. gasseri* does not change during molding and pressing.

In the production of the natural cheese, the sodium chloride is added to a cheese curd, a surface of cheese or by brining into a saline solution. When brining is carried out in addition to incubation, the brining step can be carried out following the incubation step. For example, in the case of gouda cheese, the steps are as follows: 1) formation of the curd 2) molding 3) pressing 4) incubation of the curd 5) addition of sodium chloride by brining, and 6) preservation. The sodium chloride content in the natural cheese also affects the survival of *L. gasseri*. Since the survival of *L. gasseri* is restricted at a high sodium chloride concentration, the sodium chloride concentration is preferably 3% or less, preferably 2% or less per g cheese.

Similarly, the survival of *L. gasseri* is restricted in the presence of oxygen. It is therefore preferable to mature and preserve the cheese after vacuum-packing, inert gas-purged packing or sealing the surface with wax, a plastic film or the like.

The natural cheese of the present invention may contain a food or liquid which can be added to cheese, a sweetener, an acidifier, a seasoning, a spices, a flavor, a vitamin, and other food additives which can be added to cheese.

In the thus obtained product, *L. gasseri* grows in a sufficient amount in the cheese and *L. gasseri* survives at a high concentration after maturing and preservation. Thus, a cheese having a disinfection potency against *H. pylori* can be obtained according to the present invention.

The present invention is explained in further detail with reference to Examples and Test Examples but the present invention is not limited thereto.

Example 1

Process of Producing Cheddar *L. gasseri*-Containing Cheese

*L. gasseri* OLL 2716 (FERM BP-6999) and a marketed lactic acid bacteria mixture for cheese (O-180, available from Hansen) were each inoculated at a ratio of 1% into a 10% skim milk medium. Then *L. gasseri* was cultured at 37° C. for 17 hours while O-180 was cultured at 25° C. for 17 hours, thereby giving bulk starters. Subsequently, 100 kg of milk, which had been sterilized at 73° C. for 15 seconds, was adjusted to 30° C. and inoculated with 1% of each the *L. gasseri* and the O-180 bulk starter as described above. Then 10 kg of cheddar cheese of about 30 cm in length and width and about 10 cm in height was produced by a conventional method. This cheddar cheese was vacuum-packed in an Eval coat nylon polyethylene film (manufactured by Mitsubishi Plastics, Inc.) and preserved at 5° C. and 10° C. The *L. gasseri* count and the count of other bacteria in each step and the bacterial count for 6 months from the day after production, at intervals of 1 month, were examined in accordance with the following bacterium examination method (Tables 1 and 2). The same method was employed in each of the bacterium examinations carried out hereinafter. The bacterial counts of the cheddar cheese were measured at the center and at the surface part (the part of up to 5 mm in depth from the surface).

As a result, *L. gasseri* increased to $5 \times 10^8$ cfu/g (8.7 log cfu/g) at the maximum level and its bacterial count was maintained at a level of $10^8$ cfu/g (8.0 log cfu/g) or more for 3 months (when preserved at 5° C.) or for 1 month (when preserved at 10° C.). When preserved for 6 months, $10^7$ cfu/g (7.0 log cfu/g) or more of cells survived both the preservations at 5° C. and 10° C. (Table 2, FIG. 1). When about 10 g of cheese is taken in a single dose and thus the cheese is packed in 10 g portions (package unit), the maximum bacterial count 3 months after the production corresponds to $2 \times 10^9$ cfu/package (9.3 log cfu/package) and the maximum bacterial count 6 months after the production corresponds to $4 \times 10^8$ cfu/package (8.6 log cfu/package). It has been thus confirmed that the intake of about 10 g of the cheese enables the maintenance of a sufficient bacterial count for disinfecting *H. pylori* and/or protecting against infection with *H. pylori*. The thus obtained cheddar cheese contained 42% moisture, 28% fat, 26% protein and 0.9% sodium chloride. Since it contained a small amount of sodium chloride, it showed a little saltiness and sourness. After maturing, it showed a slight bitterness, although no serious problem was caused thereby (Table 3).

Bacterium Examination Method:

Medium:

In 100 ml of water, 6 g of BL agar medium (manufactured by Eiken Chemical Co., Ltd.) was dissolved and sterilized in an autoclave at 121° C. for 15 minutes. Then it was cooled to about 50° C. and equine defibrinated blood (manufactured by Nippon Biotest) was aseptically added to give a concentration of 5%. After mixing, the mixture was dispensed into Petri dishes to form a plate medium which was used in measuring the bacterial count.

Dilution Method:

After dissolving the curd in 10-folds volume of a 2% disodium hydrogen phosphate solution, a cheese sample was diluted directly with physiological saline. Samples other than cheese were diluted directly with physiological saline to give a desired concentration. Then 0.1 ml of each sample was coated on the BL-plate medium containing equine defibrinated blood described above and cultured under aerobic conditions at 35° C. for 3 days. Then the viable *L. gasseri* cells and other bacteria were counted.

Criteria for Counting Colonies:

(1) *L. gasseri*

Regular to somewhat irregular round, dark brown, rough and large colonies were separately counted as *L. gasseri*.

(2) Other Bacteria

Colonies of other bacteria were slightly rising, dark brown, smooth and small. These bacteria were indicated as the sum excluding the *L. gasseri* count.

TABLE 1

Changes in bacterial count during the process for producing *L. gasseri* OLL 2716-containing cheddar cheese

| Step | *L. gasseri* count (log cfu/g) | Other bacteria (log cfu/g) |
|---|---|---|
| Sterilized milk | —[1] | 3.40 |
| *L. gasseri* starter | 8.00 | — |
| O-180 starter | — | 8.00 |
| Raw milk with starter | 6.00 | 6.30 |
| Whey | 6.00 | 6.30 |
| Salt-free curd (Day Produced) | 8.71 | 9.23 |
| Salt-containing curd (Day Produced) | 8.79 | 9.28 |
| Day following production | 8.74 | 9.27 |

Note
[1]Not measured (the same applies hereinafter).

TABLE 2

Changes in bacterial count during preservation of *L. gasseri* OLL 2716-containing cheddar cheese

| Preservation temperature | Preserved at 10° C. (log cfu/g) | | | | Preserved at 5° C. (log cfu/g) | |
|---|---|---|---|---|---|---|
| Sampling part | Center | | Surface | | Center | |
| Preservation time | LG | Others | LG | Others | LG | Others |
| Immediately after production | 8.79 | 9.28 | 8.79 | 9.27 | — | — |
| Day following production | 8.74 | 9.27 | 8.71 | 9.27 | — | — |
| After 1 week | 8.69 | 9.46 | 8.60 | 9.44 | — | — |
| After 2 weeks | 8.72 | 9.68 | 8.60 | 9.66 | — | — |
| After 1 month | 8.30 | 9.11 | 8.60 | 9.43 | 8.54 | 9.42 |
| After 2 months | 7.48 | 8.41 | — | — | 8.60 | 9.26 |
| After 3 months | 8.00 | 8.26 | — | — | 8.30 | 9.00 |
| After 4 months | 7.70 | 7.85 | — | — | 7.95 | 8.49 |
| After 5 months | 7.85 | 8.32 | — | — | 7.85 | 8.32 |
| After 6 months | 7.58 | 7.86 | — | — | 7.61 | 8.05 |

LG: *L. gasseri*

TABLE 3

Components and flavor of *L. gasseri* OLL 2716-containing cheddar cheese

| Item | Next day | After 1 month | After 6 months |
|---|---|---|---|
| pH | 5.10 | 5.12 | 5.23 |
| Moisture (%) | — | 41.82 | — |
| Sodium chloride (%) | — | 0.90 | — |
| Flavor | — | Somewhat sour | Slightly bitter |

Example 2

Process for Producing *L. gasseri*-Containing Gouda Cheese

Figure 2:
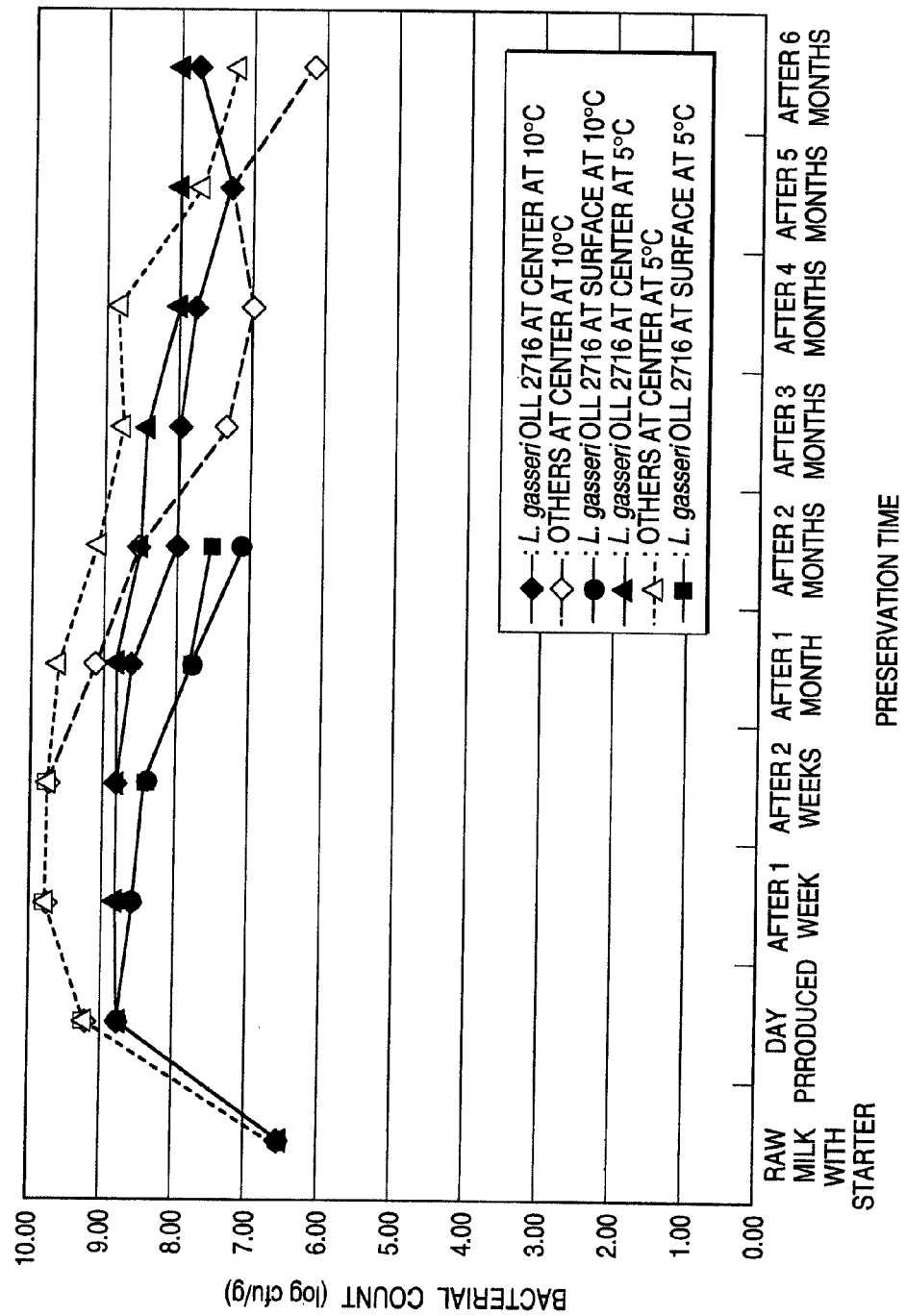
FIG. 2 shows bacterial count changes in *L. gasseri*-containing gouda cheese (Example 2).

*L. gasseri* OLL 2716 and a marketed lactic acid bacteria mixture for cheese (CHN-01, available from Hansen) were each inoculated at a ratio of 1% into a 10% skim milk medium. Then *L. gasseri* was cultured at 37° C. while CHN-01 was cultured at 25° C. each for 17 hours, thereby giving bulk starters. Subsequently, 100 kg of partially skim milk (SNF 8.5%, fat 3%), which had been sterilized at 73° C. for 15 seconds, was adjusted to 32° C. and inoculated with 1% of each of the *L. gasseri* bulk starter and the CHN-01 bulk starter. Then 10 kg of gouda cheese of about 30 cm in length and width and about 10 cm in height was produced by a conventional method. Table 4 shows bacterial counts in respective steps. The obtained gouda cheese contained 43% moisture, 24% fat, 25% protein and 1.7% sodium chloride. This gouda cheese was vacuum-packed in an Eval coat nylon polyethylene film and preserved at 5° C. and 10° C. The *L. gasseri* count and the count of other bacteria were examined for 6 months from the day after packing at intervals of 1 month. In the gouda cheese, *L. gasseri* also increased to $6 \times 10^8$ cfu/g (8.8 log cfu/g) at the maximum level. At the center of the cheese, the bacterial count was maintained at a level of $10^8$ cfu/g (8.0 log cfu/g) or more for 3 months (when preserved at 10° C.) or for 6 months (when preserved at 5° C.). When preserved at 10° C. for 6 months, $10^7$ cfu/g (7.0 log cfu/g) or more of cells survived. In the surface part (the part of up to 5 mm in depth from the surface), the bacterial count decreased faster and attained $10^7$ cfu/g (7.0 log cfu/g) within 1 month and $10^6$ cfu/g (6.0 log cfu/g) or less after 6 months (Table 5, FIG. 2). No problem was noticeable concerning the flavor of the gouda cheese (Table 6).

TABLE 4

Changes in bacterial count during the process of producing
L. gasseri OLL 2716-containing gouda cheese

| Step | L. gasseri count (log cfu/g) | Other bacteria (log cfu/g) |
|---|---|---|
| Sterilized milk | — | 3.48 |
| L. gasseri starter | 9.03 | — |
| CHN-01 starter | — | 9.03 |
| Raw milk with starter | 6.79 | 6.92 |
| Whey | 6.08 | 6.04 |
| Salt-free curd (Day produced) | 8.74 | 9.23 |
| Salt-containing curd (Day following production) | 8.75 | 9.69 |

TABLE 5

Changes in bacterial count during preservation of
L. gasseri OLL 2716-containing gouda cheese

| Preservation temperature | Preserved at 10° C. (log cfu/g) | | | | Preserved at 5° C. (log cfu/g) | | | |
|---|---|---|---|---|---|---|---|---|
| Sampling part | Center | | Surface | | Center | | Surface | |
| Preservation time | LG | Others | LG | Others | LG | Others | LG | Others |
| Immediately after production | 8.75 | 9.69 | 8.74 | 9.67 | — | — | — | — |
| After 1 week | 8.78 | 9.74 | 8.60 | 9.66 | — | — | — | — |
| After 2 weeks | 8.81 | 9.77 | 8.38 | 8.76 | — | — | — | — |
| After 1 month | 8.60 | 9.04 | 7.78 | 8.73 | 8.78 | 9.62 | 7.78 | 8.73 |
| After 2 months | 8.00 | 8.60 | 7.10 | 8.42 | 8.60 | 9.20 | 7.48 | 8.70 |
| After 3 months | 8.08 | 7.41 | — | — | 8.38 | 8.75 | — | — |
| After 4 months | 7.60 | 7.04 | — | — | 8.04 | 8.86 | — | — |
| After 5 months | 7.38 | 7.36 | — | — | 8.04 | 7.79 | — | — |
| After 6 months | 7.67 | 6.20 | <6.00 | <6.00 | 8.01 | 7.30 | <6.00 | <6.00 |

LG: L. Gasseri

TABLE 6

Components and flavor of L. gasseri OLL 2716-containing gouda cheese

| Item | Next day | After 1 month | After 6 months |
|---|---|---|---|
| pH | 5.18 | 5.29 | 5.23 |
| Moisture (%) | — | 43.36 | — |
| Sodium chloride (%) | — | 1.70 | — |
| Flavor | — | Somewhat sour | Somewhat sour |

Example 3

Process for Producing L. gasseri-Enriched Gouda Cheese (2)

L. gasseri OLL 2716 was inoculated at a ratio of 1% into a 10% skim milk medium containing 0.1% yeast extract (manufactured by Difco), while a marketed lactic acid bacteria for cheese Lactococcus lactis subsp. lactis (isolated from CHN-01, available from Hansen) was inoculated at a ratio of 1% into a 10% skim milk medium. Then L. gasseri was cultured at 37° C. for 24 hours and L. lactis was cultured at 25° C. for 17 hours, thereby giving bulk starters. Subsequently, 20 kg of partially skim milk (SNF 8.5%, fat 3%), which had been sterilized at 73° C. for 15 seconds, was adjusted to 32° C. and inoculated with 1% of each of the L. gasseri bulk starter and the L. lactis bulk starter. Next, 20 g of yeast extract was further added. Then cheese curd was produced by a conventional method, pressed and incubated in a mold in a room at a room temperature of 25° C. for 24 hours. After taking out from the mold, the cheese was immersed in a 20% saline solution at 10° C. for 24 hours. Thus 2 kg of a ring-type gouda cheese of about 20 cm in diameter and about 8 cm in height was produced. Table 7 shows bacterial counts of L. gasseri and other bacteria in respective steps. This gouda cheese was vacuum-packed in an Eval coat nylon polyethylene film and preserved at 5° C. and 10° C. The L. gasseri count and the count of other bacteria were examined for 6 months from the day after packing at intervals of 1 month.

Figure 3:
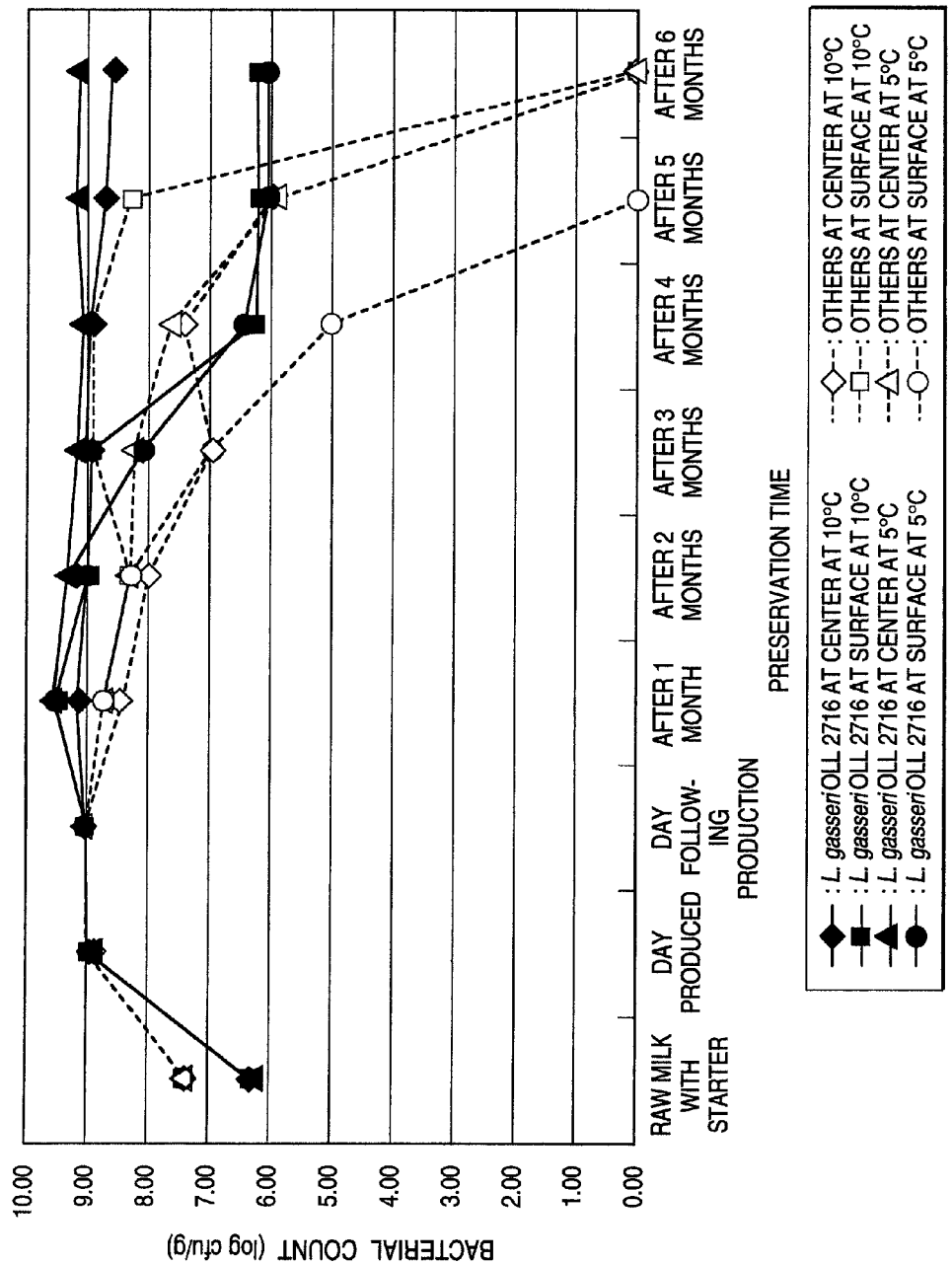
FIG. 3 shows bacterial count changes in *L. gasseri*-enriched gouda cheese (Example 3).

As a result, L. gasseri remarkably proliferated from the day of the production. It was confirmed that the bacterial count at the center of the L. gasseri-containing cheese was maintained at $10^8$ cfu/g (8.0 log cfu/g) or more for 6 months (Table 8, FIG. 3). On the day of production, the L. gasseri count was almost the same as the count of other bacteria. From the following day, L. gasseri alone proliferated and the L. gasseri count was maintained at a higher level than the count of other bacteria 3 months after the production. Namely, it was confirmed that the growth of L. gasseri was enhanced by adding a yeast extract before the production of the curd and incubating the obtained curd after pressing in addition to the process for producing gouda cheese in Example 2. The thus obtained gouda cheese contained 40% moisture, 26% fat, 26% protein and 1.5% sodium chloride. No problem was noticeable concerning its flavor (Table 9).

TABLE 7

Changes in bacterial count during the process of producing
L. gasseri OLL 2716-enriched gouda cheese

| Step | L. gasseri count (log cfu/g) | Other bacteria (log cfu/g) |
|---|---|---|
| Sterilized milk | — | 3.26 |
| L. gasseri starter | 8.95 | — |
| L. lactis starter | — | 8.60 |
| Raw milk with starter | 6.30 | 7.40 |
| Whey | 8.76 | 8.97 |
| Salt-free curd (Day Produced) | 8.90 | 8.90 |
| Salt-containing curd (Day following production) | 9.08 | 9.08 |

TABLE 8

Changes in bacterial count during preservation of
L. gasseri OLL 2716-enriched gouda cheese

| Preservation temperature | Preserved at 10° C. (log cfu/g) | | | | Preserved at 5° C. (log cfu/g) | | | |
|---|---|---|---|---|---|---|---|---|
| Sampling part | Center | | Surface | | Center | | Surface | |
| Preservation time | LG | Others | LG | Others | LG | Others | LG | Others |
| Immediately after production | 9.08 | 9.08 | 9.08 | 9.06 | — | — | — | — |
| After 1 week | 9.08 | 8.85 | 9.15 | 8.66 | — | — | — | — |
| After 2 weeks | 9.26 | 8.00 | 9.11 | 8.66 | 9.59 | 8.95 | — | — |
| After 1 month | 9.49 | 8.48 | 9.18 | 8.70 | 9.53 | 8.90 | 9.53 | 8.90 |
| After 2 months | 9.00 | 8.00 | 8.90 | 8.30 | 9.30 | 8.30 | 9.30 | 8.23 |
| After 3 months | 9.06 | 7.00 | 8.87 | 8.87 | 9.23 | 8.30 | 8.08 | 7.00 |
| After 4 months | 8.93 | 7.48 | 6.30 | 8.91 | 9.11 | 7.70 | 6.48 | 5.00 |
| After 5 months | 8.74 | 6.00 | 6.26 | 8.30 | 9.18 | 6.00 | 6.11 | — |
| After 6 months | 8.58 | — | 6.18 | — | 9.11 | — | 6.08 | — |

LG: L. gasseri

TABLE 9

Components and flavor of L. gasseri OLL 2716-enriched gouda cheese

| Item | Next day | After 1 month | After 3 months | After 6 months |
|---|---|---|---|---|
| pH | 5.37 | 5.02 | 5.18 | 5.25 |
| Moisture (%) | — | 40.02 | — | — |
| Sodium chloride (%) | — | 1.51 | — | — |
| Flavor | — | Good | Good | Good |

Example 4

Process for Producing L. gasseri-Containing String Cheese

Figure 4:
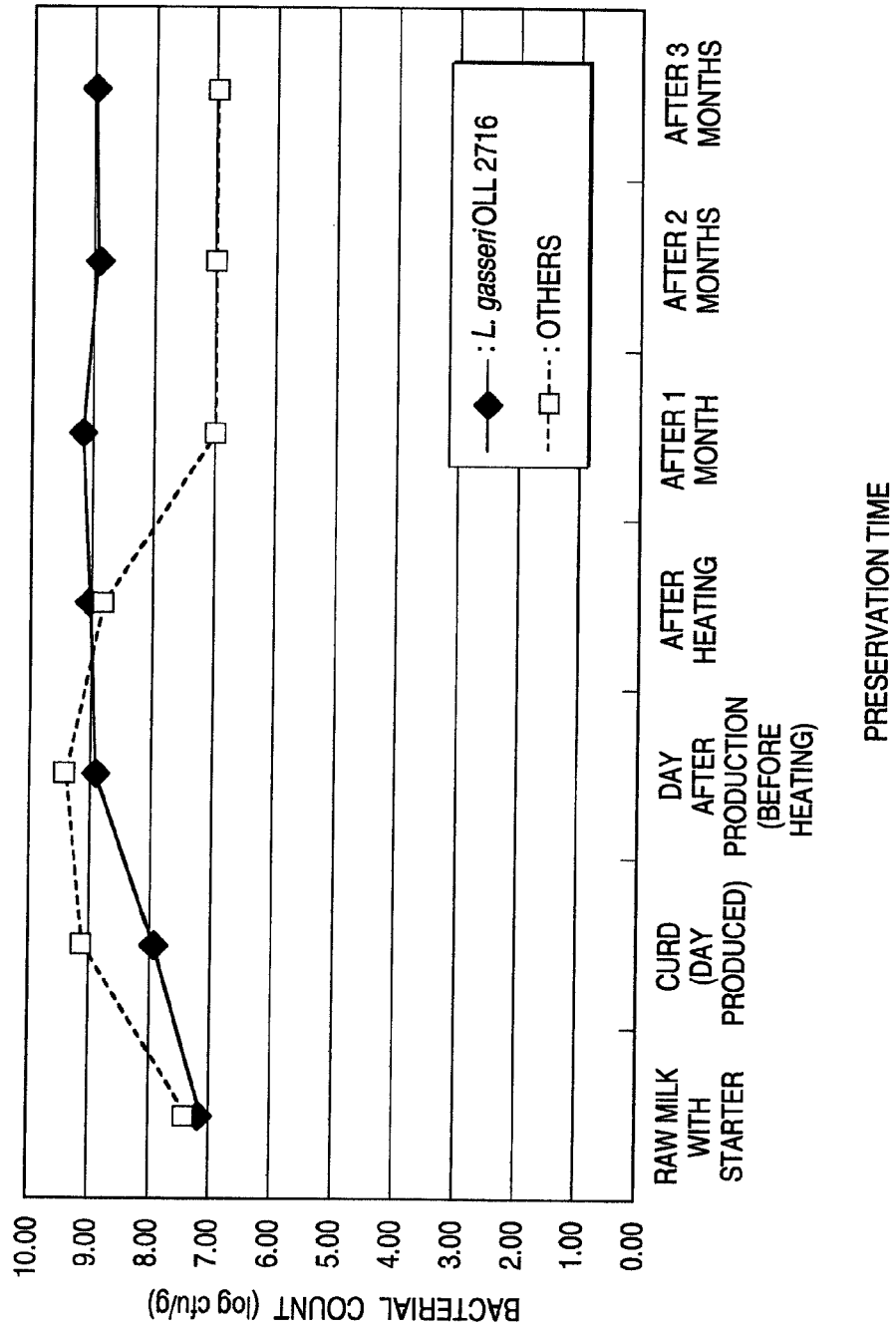
FIG. 4 shows bacterial count changes in *L. gasseri*-containing string cheese (Example 4).

On the day following production, 2 kg of the cheese curd obtained in Example 3 before immersing in saline was cut into cubes of 2 cm on a side, put into a fine-mesh metallic wire basket and then immersed in 10 kg of water at 60° C. for 5 minutes. Then the cheese was taken out of water and kneaded by hand to thereby bind the curd. Then the curd was shaped into a cylinder and horizontally pulled to give a cylindrical curd of 3 cm in diameter. Then it was immediately immersed in a 20% saline solution at 2° C. for 1 hour to fix fibers. Thus fibrous cheese (string cheese) was produced. This fibrous cheese was vacuum-packed in an Eval coat nylon polyethylene film. The L. gasseri count and the count of other bacteria were examined for 3 months from the day after packing at intervals of 1 month. Thus, it was confirmed that the L. gasseri count was maintained at a level of $10^8$ cfu/g (8.0 log cfu/g) or above for 3 months starting from the day after production (FIG. 4). The string cheese showed excellent flavor and fiber texture (Table 10).

TABLE 10

Components and flavor of L. gasseri OLL 2716-containing string cheese

| Item | Next day | After 1 month | After 3 months |
|---|---|---|---|
| pH | 5.23 | 5.28 | 5.35 |
| Moisture (%) | — | 43.32 | — |
| Sodium chloride (%) | — | 1.3 | — |
| Flavor | Bland | Good | Good |
| Fiber texture | Strong | Strong | Recognized |

Example 5

Anti-H. pylori Effect of L. gasseri-Containing Cheese

Figure 5:
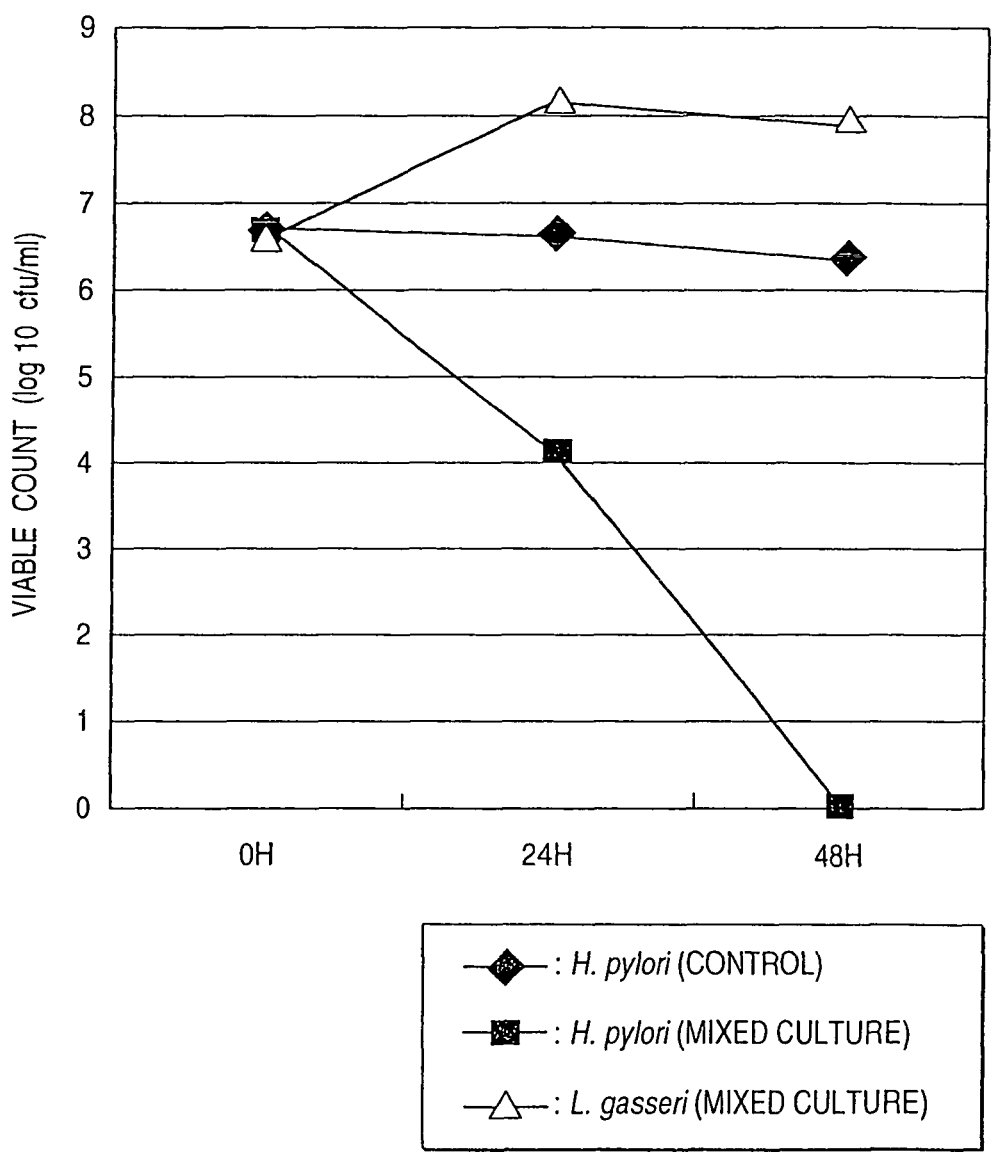
FIG. 5 shows anti-*H. pylori* effect of *L. gasseri*-containing cheese (Example 5), wherein ■ and Δ stand for the viable counts of *H. pylori* and *L. gasseri*, respectively, when *L. gasseri*-containing cheese was cultured together with *H. pylori*; and ♦ stands for the viable count of *H. pylori* when *L. gasseri*-free cheese is cultured together with *H. pylori* (control).

To 5 g of the L. gasseri-containing cheese produced in Example 3 which had been vacuum-packed in an Eval coat nylon polyethylene film and preserved at 5° C. for 5 months, 45 g of physiological saline was added thereto and the obtained mixture was well mixed in a blender (trade name: Lab-Blender 400, available from A.J. Seward). To 5 ml of the liquid mixture, 50 ml of Brucella broth adjusted to pH 6, 2.5 ml of FCS (fetal calf serum) and 5 ml of H. pylori culture which had been cultured separately were added, followed by culturing at 37° C. under slightly aerobic conditions. As a control, another gouda cheese produced without adding L. gasseri and preserved in the same manner was also tested. The H. pylori count and the L. gasseri count were measured 0, 24 and 48 hours after the initiation of the culture. When cultured with L. gasseri-containing cheese, as a result, H. pylori was decreased to a level lower than the detection limit after 48 hours (FIG. 5).

Test Example 1

Salt-Tolerance Test of L. gasseri

Figure 6:
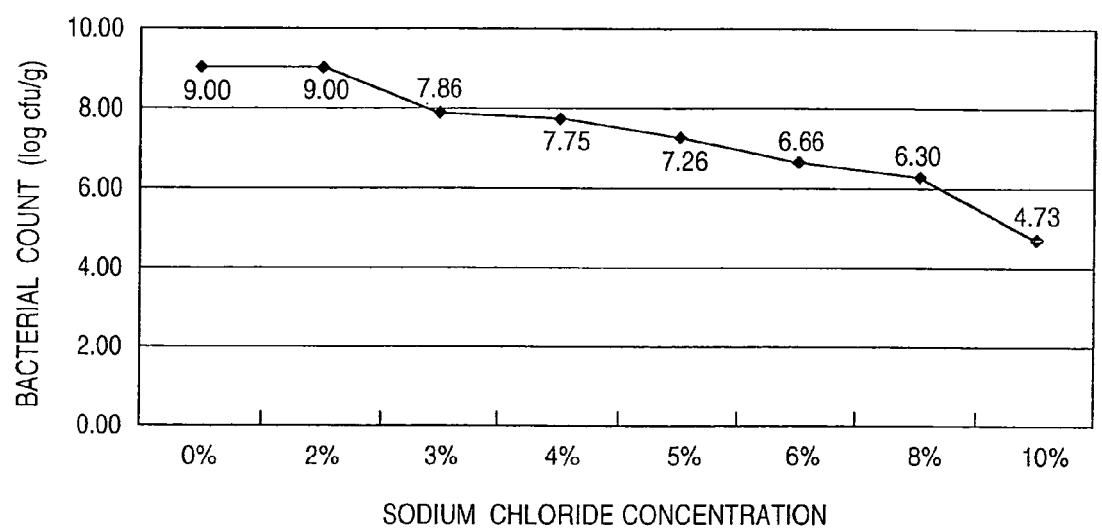
FIG. 6 shows the salt-tolerance of *L. gasseri* (Test Example 1).

Into test tubes, a 10% skim milk medium prepared so as to give sodium chloride concentrations of 2 to 10% (mixed with sodium chloride after autoclaving) were dispensed and inoculated with the L. gasseri OLL 2716 to give a concentration of $2 \times 10^7$ cfu/g. After statically culturing at 35° C. for 24 hours, the bacterial counts were measured. At a sodium chloride concentration of 2%, the bacteria proliferated without any problem. At a sodium chloride concentration of 3 to 4%, the bacteria proliferated moderately. At a sodium chloride concentration of 5%, the bacteria were almost in the static state. At a sodium chloride concentration of 6% or above, the bacterial count was decreased. In terms of sodium chloride/moisture ratio in cheese, the above results mean that the bacteria proliferated without any problem at a sodium chloride content cheese of 0.5%, it somewhat proliferated at 1%, it remained static at 1.25% and the bacterial count decreased at 1.5% or above. It has been thus confirmed that in gouda cheese to which a brine is added, it is preferable to control the sodium chloride content to 2% or less (FIG. 6).

Test Example 2

Growth of Various Strains Under Acidic Conditions

Each 10 µl of various lactic acid bacteria cultured twice for activation by using MRS Broth at 37° C. for 18 hours was inoculated to a modified MRS Broth prepared by dissolving NaCl of 0.2% and pepsin (1:5000; manufactured by Tokyo Kasei Kogyo Co.) of 0.35% into MRS Broth and adjusting the pH to 4.0, followed by culturing aerobically at 37° C. The turbidity ($OD_{650}$) of each medium was measured just after the initiation of culturing and 9 hours after the initiation of culturing, thereby the increase of turbidity ($\Delta OD_{650}$) being measured.

In this manner, the growth of strains having a high resistance against an artificially-prepared gastric juice was tested at the low pH value. As a result, high growth was shown by *L. gasseri* OLL 2716 and *L. gasseri* No. 6; *L. gasseri* OLL 2716 showed the highest growth.

Figure 7:
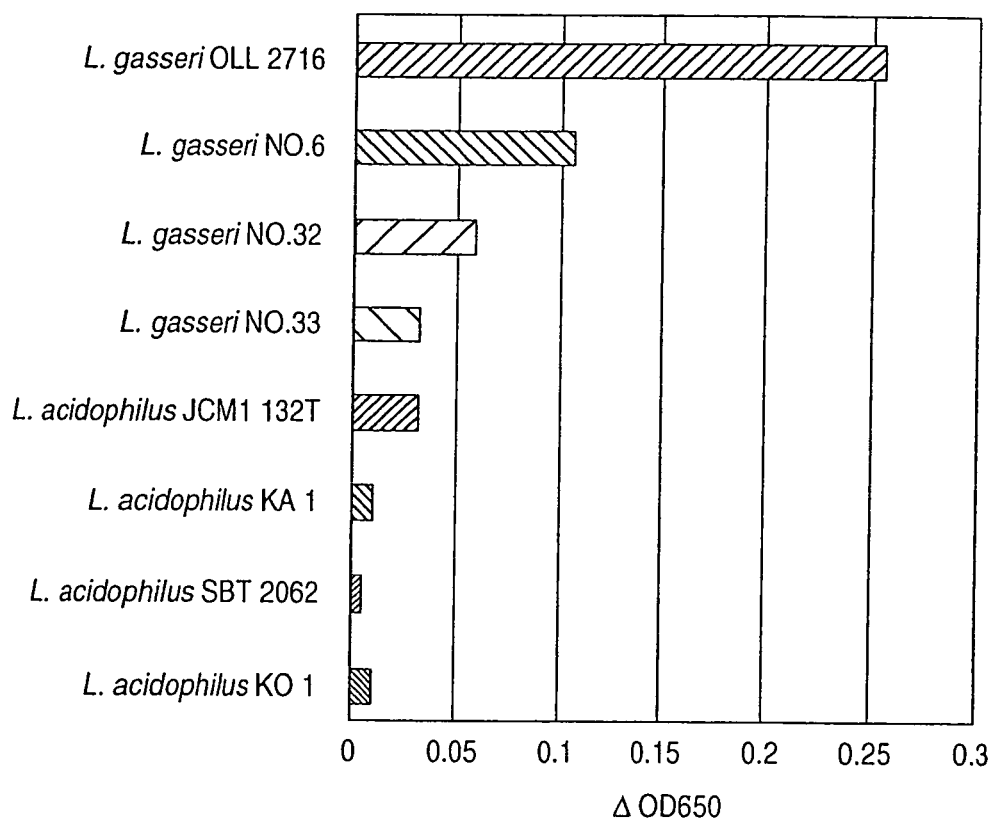
FIG. 7 shows growth of various *Lactobacillus* bacteria under acidic conditions (Test Example 2).

The results are shown in FIG. 7.

Test Example 3

Effect of Lactic Acid Bacteria on Mice Infected with *H. pylori*

*H. pylori* NCTC 11637 was administered orally to infect germ free mice (BALB/c) at $1 \times 10^9$ cfu/mouse once a day for three days. After 4 weeks passed from the administration of the *H. pylori*, *L. gasseri* OLL 2716, *L. gasseri* No. 6 and *L. salivarius* WB1004 were, respectively, administered orally to *H. pylori*-infected mice at $1 \times 10^9$ cfu/mouse once a week during the 1st week to the 7th week. Eight weeks after the administration of the lactic acid bacteria, the number of *H. pylori* in their stomachs was measured, and serum anti-*H. pylori* antibody titer was assayed.

Eight weeks after the administration of the lactic acid bacteria, the number of *H. pylori* in the stomach of the control mice administered *H. pylori* alone was detected at $1 \times 10^5$ cfu/g of stomach contents, while the number of *H. pylori* in the stomachs of mice administered with *L. gasseri* OLL 2716 and *L. salivarius*, respectively, decreased below the detectable limit ($1 \times 10^3$ cfu/g of stomach contents). The serum anti-*H. pylori* antibody titer in the mice administered with *L. gasseri* OLL 2716 was the lowest.

Thus, it was observed that *L. gasseri* OLL 2716 showed the highest effect to disinfect *H. pylori* in the stomachs of the mice infected with *H. pylori*.

Figure 8:
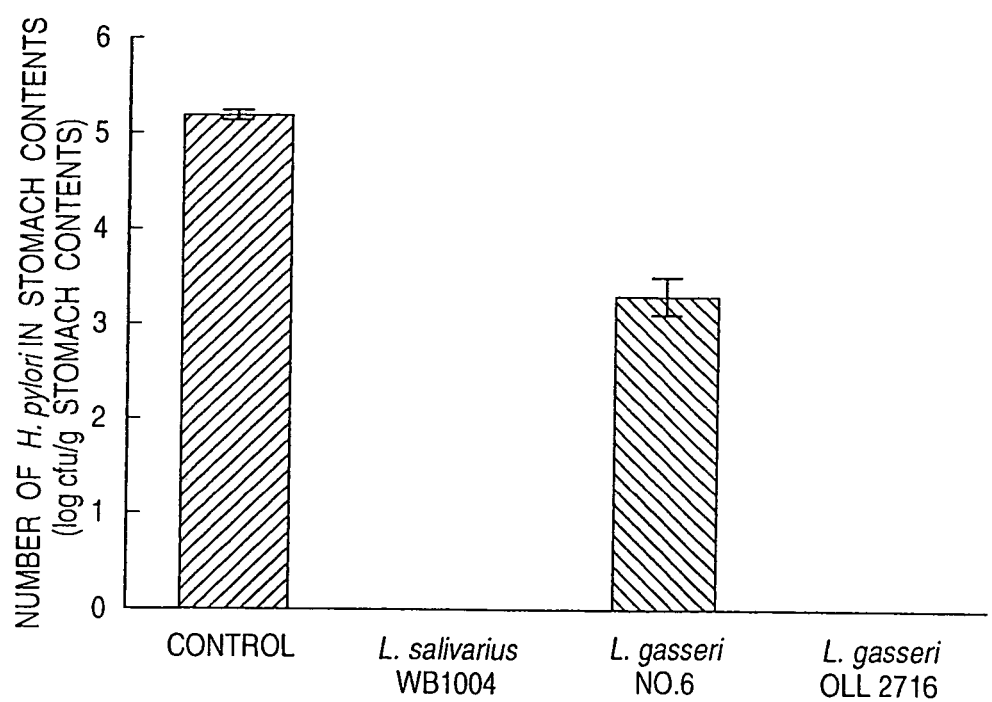
FIG. 8 shows number of *H. pylori* in stomach contents (Test Example 3).
Figure 9:
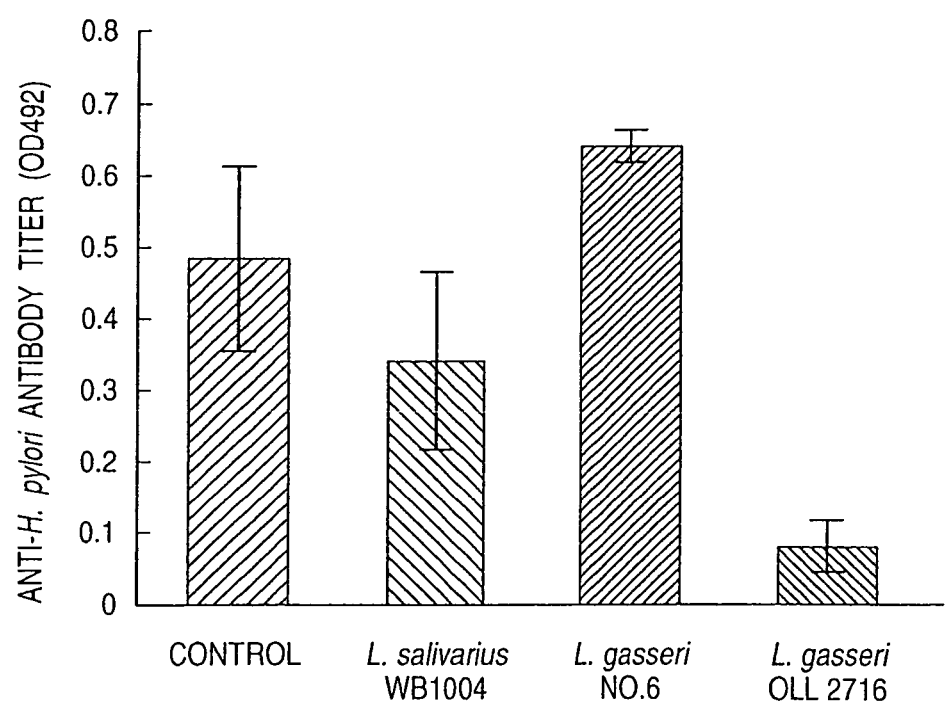
FIG. 9 shows anti-*H. pylori* antibody titer (Test Example 3).

The results are shown in FIG. 8 and FIG. 9.

While the invention has been described in detail and with reference to specific embodiments thereof, it will be apparent to one skill in the art that various changes and modifications can be made therein without departing from the spirit and scope thereof. All references cited herein are incorporated in their entirety.

This application is based on Japanese application No. 2002-111083 filed on Apr. 12, 2002 and No. 2002-213338 filed on Jul. 23, 2002, the entire contents of which are incorporated hereinto by reference.

INDUSTRIAL APPLICABILITY

According to the present invention, it is possible to obtain natural cheese containing a lactic acid bacterium belonging to *L. gasseri* which has a high disinfection potency against *H. pylori*, is resistant to low pH environment and shows a high survival ratio. In this natural cheese, viable *L. gasseri* cells can be maintained over a prolonged period of time. Moreover, it can be orally administered as such, similar to general natural cheeses. Thus, the cheese can be ingested by healthy people as well as babies and infants, aged people, valetudinarians, and convalescents and the like for a long period of time and exerts a particularly excellent prophylactic and/or therapeutic effect of gastritis, gastric ulcer and the like.

As described above, an *L. gasseri* count can be maintained at a sufficient level by employing standard production conditions or preservation conditions in producing or preserving cheese. Furthermore, when a step of addition of an yeast extract and/or a step of incubating the curd after molding and pressing is added to the above production process, the proliferation activity and survival of *L. gasseri* can be further enhanced. Thus, *L. gasseri* grows in cheese dominantly over other lactic acid bacteria and the bacterial count can be maintained for a long period of time. Thus, *L. gasseri* can be sufficiently ingested in a necessary bacterial count even with only small food intake. The present invention can also be considered as highly useful from this viewpoint.

The invention claimed is:

1. A process for producing a natural cheese, which comprises:
   (1) incubating a lactic acid bacteria starter with a culture medium containing milk to which yeast extract is added, wherein the lactic acid bacteria starter comprises a lactic acid bacterium belonging to *Lactobacillus gasseri* having a disinfection potency against *Helicobacter pylori*;
   (2) adding the incubated lactic acid bacteria starter to a raw milk;
   (3) forming a curd from the raw milk mixed with the lactic acid bacteria starter;
   (4) removing whey from thus formed curd; and
   (5) forming pressed pieces of the curd including molding and pressing the curd,
   wherein the process further comprises
   adding additional yeast extract to the raw milk at the same time or after adding the lactic acid bacteria starter to the raw milk in step (2), and before formation of the curd in step (3); and
   incubating the curd obtained in the above (5), at 20 to 35° C. for 16 to 26 hours to produce the natural cheese, wherein the incubation of the curd is carried out without cooling the curd after molding and pressing; and
   wherein the additional yeast extract added is in an amount of 0.05 to 0.2 wt %;
   wherein the natural cheese comprises the lactic acid bacterium belonging to *Lactobacillus gasseri* having a disinfection potency against *Helicobacter pylori*, wherein the natural cheese has a viable cell count of *Lactobacillus gasseri* in the number of $10^7$ cfu/g or more when preserved at a temperature of 10° C. or less for 6 months.

2. The process according to claim 1, wherein the lactic acid bacteria starter is a mixture of the lactic acid bacterium belonging to *Lactobacillus gasseri* having a disinfection potency against *Helicobacter pylori* and another strain of lactic acid bacterium.

3. The process according to claim 1, wherein the lactic acid bacterium is *Lactobacillus gasseri* OLL 2716 (FERM BP-6999).

* * * * *